US012629385B2

(12) United States Patent
Duan

(10) Patent No.: US 12,629,385 B2
(45) Date of Patent: May 19, 2026

(54) STABLE AST-3424 INJECTION PREPARATION AND PREPARATION METHOD

(71) Applicant: OBI PHARMA, INC., Taipei City (TW)

(72) Inventor: Jianxin Duan, Guangdong (CN)

(73) Assignee: OBI PHARMA, INC., Taipei City (TW)

(*) Notice: Subject to any disclaimer, the term of this patent is extended or adjusted under 35 U.S.C. 154(b) by 1113 days.

(21) Appl. No.: 17/626,962

(22) PCT Filed: Jul. 14, 2020

(86) PCT No.: PCT/CN2020/101870
§ 371 (c)(1),
(2) Date: Jan. 13, 2022

(87) PCT Pub. No.: WO2021/008520
PCT Pub. Date: Jan. 21, 2021

(65) Prior Publication Data

US 2023/0181606 A1 Jun. 15, 2023

(30) Foreign Application Priority Data

Jul. 15, 2019 (CN) ......................... 201910635633.2

(51) Int. Cl.

| | |
|---|---|
| ***A61K 31/67*** | (2006.01) |
| ***A61J 1/06*** | (2006.01) |
| ***A61J 1/14*** | (2023.01) |
| ***A61K 9/08*** | (2006.01) |
| ***A61K 31/675*** | (2006.01) |
| ***A61K 47/02*** | (2006.01) |
| ***A61K 47/10*** | (2017.01) |

(52) U.S. Cl.
CPC ............. *A61K 31/675* (2013.01); *A61J 1/065* (2013.01); *A61J 1/1468* (2015.05); *A61K 9/08* (2013.01); *A61K 47/02* (2013.01); *A61K 47/10* (2013.01)

(58) Field of Classification Search
CPC .................................................... A61K 31/675
See application file for complete search history.

(56) References Cited

U.S. PATENT DOCUMENTS

2018/0044360 A1 2/2018 Duan et al.

FOREIGN PATENT DOCUMENTS

| | | | |
|---|---|---|---|
| CN | 1600314 | A | 3/2005 |
| CN | 101829078 | A | 9/2010 |
| CN | 107530556 | A | 1/2018 |
| CN | 108290911 | A | 7/2018 |
| CN | 111568759 | A | 8/2020 |
| CN | 111573604 | A | 8/2020 |
| JP | 2018-513876 | A | 5/2018 |
| JP | 2018-517710 | A | 7/2018 |
| KR | 10-2017-0130615 | A | 11/2017 |
| TW | 201706262 | A | 2/2017 |
| TW | 201726695 | A | 8/2017 |
| WO | WO03/037314 | A2 | 5/2003 |
| WO | WO 2016/145092 | A1 | 9/2016 |
| WO | WO 2017/087428 | A1 | 5/2017 |
| WO | WO2019/062919 | A1 | 4/2019 |

OTHER PUBLICATIONS

Evans et al., "OBI-3424, a Novel AKR1C3-Activated Prodrug, Exhibits Potent Efficacy against Preclinical Models of T-ALL," Clinical Cancer Research, vol. 25, No. 14, 2019, pp. 4493-4503.
Strickley, "Solubilizing Excipients in Oral and Injectable Formulations," Pharmaceutical Research, vol. 21, No. 2, 2004, pp. 201-230.
International Search Report for PCT Patent App. No. PCT/CN2020/101870 (Oct. 15, 2020).
Lock, R. B., et al., "Abstract LB-B16: The AKR1C3-Activated Prodrug OBI-3424 Exerts Profound In Vivo Efficacy Against Preclinical Models of T-Cell Acute Lymphoblastic Leukemia (T-ALL); a Prediatric Preclinical Testing Consortium Study," Abstracts; AACR-NCI-EORTC International Conference: Molecular Targets and Cancer Therapeutics; Oct. 26-30, 2017, Philadelphia PA, 4 pp.
Evans, K., et al., "OBI-3424, a novel AKR1C3-acivated prodrug, exhibits potent efficacy against preclinical models of T-ALL," downloaded from clincancerres.aacrjournals.org on Apr. 25, 2019, American Association of Cancer Research, 33 pp.
Zhang, Q., et al., "Injection," Pharmaceutics, 2005, 80 pp.

*Primary Examiner* — Shawquia Jackson
(74) *Attorney, Agent, or Firm* — Birch, Stewart, Kolasch & Birch, LLP

(57) ABSTRACT

A stable AST-3424 injection preparation, being a solution containing 0.1-200 mg/ml or 1-200 mg/ml of AST-3424 active pharmaceutical ingredient. A solvent in the solution contains a C2-C8 monohydric alcohol. The preparation method comprises the following steps: subjecting the AST-3424 active pharmaceutical ingredient and a partial prescription volume of ethanol to a first dissolution and formulation; adding a prescription volume of propylene glycol for a second dissolution and formulation; and then adding the remaining prescription volume of ethanol for mixing and dissolving to obtain a solution containing 1-200 mg/ml of AST-3424 active pharmaceutical ingredient. Provided is an AST-3424 injection for injection, wherein the solvent is water, a glucose solution, ethanol, or propylene glycol, the solutes consist of the AST-3424 active pharmaceutical ingredient, an isotonic regulator, and a pH regulator. The concentration of the AST-3424 active pharmaceutical ingredient of the injection is 0.001-1.000 mg/ml, the pH of the injection is 6.8-10.5, and the solution is an isotonic solution.

18 Claims, 1 Drawing Sheet

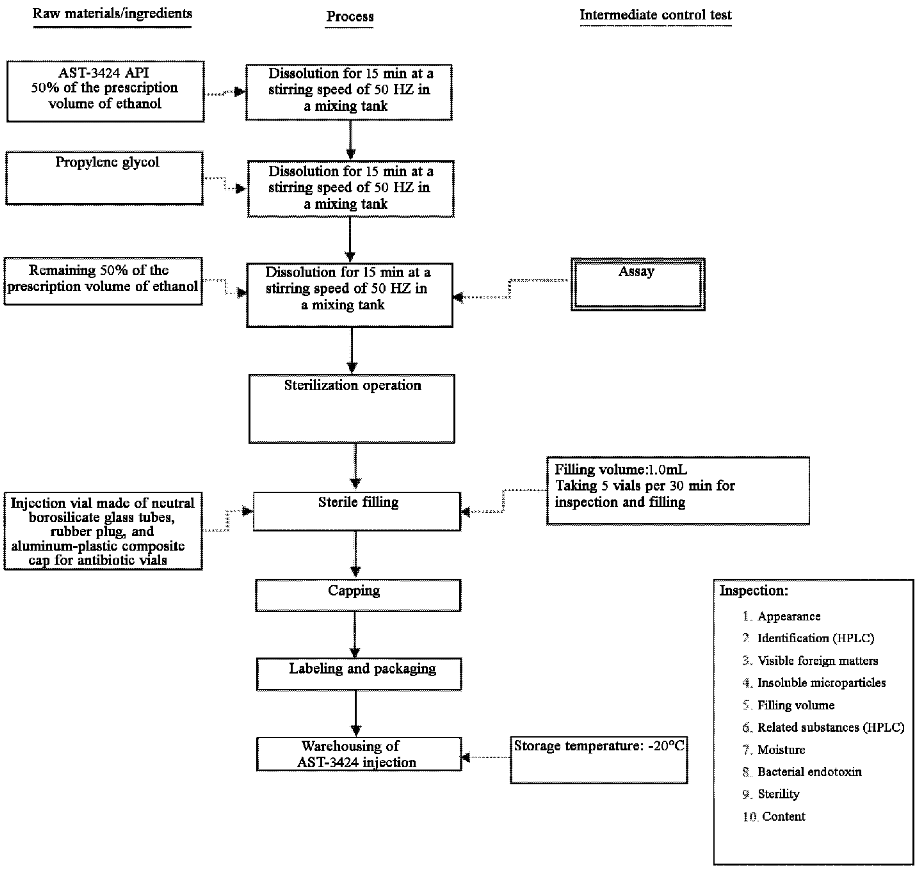
Raw materials/ingredients
Process
Intermediate control test
AST-3424 API 50% of the prescription volume of ethanol
Dissolution for 15 min at a stirring speed of 50 HZ in a mixing tank
Propylene glycol
Dissolution for 15 min at a stirring speed of 50 HZ in a mixing tank
Remaining 50% of the prescription volume of ethanol
Dissolution for 15 min at a stirring speed of 50 HZ in a mixing tank
Assay
Sterilization operation
Injection vial made of neutral borosilicate glass tubes, rubber plug, and aluminum-plastic composite cap for antibiotic vials
Sterile filling
Filling volume:1.0mL Taking 5 vials per 30 min for inspection and filling
Capping
Labeling and packaging
Warehousing of AST-3424 injection
Storage temperature: -20°C
Inspection:
1. Appearance
2. Identification (HPLC)
3. Visible foreign matters
4. Insoluble microparticles
5. Filling volume
6. Related substances (HPLC)
7. Moisture
8. Bacterial endotoxin
9. Sterility
10. Content

STABLE AST-3424 INJECTION PREPARATION AND PREPARATION METHOD

This application is a national phase entry under 35 U.S.C. § 371 of PCT Patent Application No. PCT/CN2020/101870, filed on Jul. 14, 2020, which claims priority under 35 U.S.C. § 119 to Chinese Patent Application No. 201910635633.2, filed Jul. 15, 2019, the entireties of which are incorporated by reference herein.

TECHNICAL FIELD

The present disclosure relates to the research and development of an injection of the compound disclosed in the patent application PCT/US2016/021581 with Publication No: WO2016145092A1, corresponding to the Chinese Application with Application No: 2016800150788 and Publication No: CN107530556A, and belongs to the field of the research and development of the preparations of compounds for cancer treatment.

BACKGROUND

Developed is a DNA alkylating agent AST-3424 (CAS No.: 2097713-69-2) targeting the overexpressed aldo-keto reductase 1C3 (AKR1C3) as a drug for treating cancer (see the following patent applications: "DNA ALKYLATING AGENTS", corresponding to the compound TH2870 disclosed in the PCT Application with Application No: PCT/US2016/021581 and Publication No: WO2016/145092, which corresponds to the Chinese Application with Application No: 2016800150788 and Publication No: CN107530556A; "(R)- AND (S)-1-(3-(3-N,N-DIMETHYLAMINOCARBONYL)PHENOXYL-4-NITROPHENYL)-1-ETHYL-N,N'-BIS(ETHYLENE)PHOSPHORAMIDATE, COMPOSITIONS AND METHODS FOR THEIR USE AND PREPARATION", corresponding to the S-configuration compound (name: (S)-1-(3-(3-N,N-dimethylaminocarbonyl)phenoxyl-4-nitrophenyl)-1-ethyl-N,N'-bis (ethylene)phosphoramidate, which is also referred to as OBI-3424 or S-configuration compound of TH-2870) disclosed in the PCT Application with Application No: PCT/US2016/062114 and Publication No: WO2017087428A1, which corresponds to the Chinese Application with Application No: 2016800446081 and Publication No: CN108290911A). AST-3424 has the following structure:

Chemical Structural Formula of AST-3424

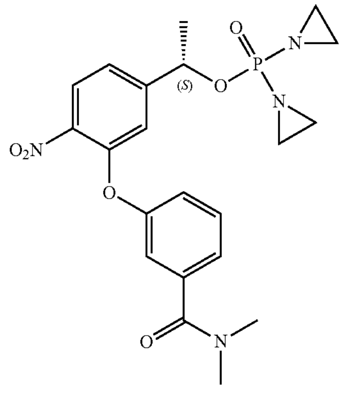

The compound has been proved to be a broad-spectrum small-molecule anticancer prodrug, and is therapeutically effective in a plurality of solid tumors and hematologic tumors by authoritative literatures in the industry (Kathryn Evans, JianXin Duan, Tara Pritchard, etal. OBI-3424, a novel AKR1C3-activated prodrug, exhibits potent efficacy against preclinical models of T-ALL[J], Clinical Cancer Research, 2019, DOI: 10.1158/1078-0432. CCR-19-0551; Richard B. Lock, Kathryn Evans, Raymond Yung, Tara Pritchard, Beverly A. Teicher, JianXin Duan, Yuelong Guo, Stephen W. Erickson and Malcolm A. Smith, Abstract LB-B16: The AKR1C3-Activated Prodrug OBI-3424 Exerts Profound In Vivo Efficacy Against Preclinical Models of T-Cell Acute Lymphoblastic Leukemia (T-ALL); a Pediatric Preclinical Testing Consortium Study [C], AACR-NCI-EORTC International Conference: Molecular Targets and Cancer Therapeutics; Oct. 26-30, 2017; Philadelphia, PA, DOI:10.1158/1535-7163.).

In order to conduct the follow-up clinical trials, there is a need to prepare a dosage form suitable for human administration: oral or injection administration in general.

During the synthesis and preparation, the substance has been found to be a yellowish liquid, which creates many difficulties in storage, transportation, and formulating preparations. The presence of amide and phosphate structures renders it inconvenient to develop tablets and oral liquid as dosage forms for oral administration. However, the R & D team has conducted preliminary experiments and found that conventional injections containing water as a solvent are not stable enough to meet the requirements for subsequent multi-center and multi-sample long-term clinical trials and commercial production and sales.

SUMMARY

The present disclosure provides a stable AST-3424 injection preparation and a preparation method therefor as well as related technologies. The injection preparation provided by such technologies has been tested to meet the requirements for long-term clinical trials and commercial production and sales. To be specific, the present application discloses the following technical solution.

The storage-stable concentrated AST-3424 injection preparation disclosed in the present disclosure is a concentrated injection of a pharmaceutical composition. The composition needs to be diluted before administration, and needs to be diluted or prepared as required, when in use, by medical staff or pharmacists or staff in pharmacies or factories.

The concentrated injection of the present disclosure may be diluted by a solution formulated by any medically acceptable isotonic regulator (as a solute) and water for injection (as a solvent).

A suitable isotonic regulator includes, but is not limited to, anhydrous or hydrous sodium chloride, glucose, sucrose, fructose, xylitol, glycerol, sorbitol, mannitol, potassium chloride, mannose, calcium chloride, magnesium chloride, and other inorganic salts. Preferably, the isotonic regulator is glucose or sodium chloride.

Provided is a stable AST-3424 injection preparation, which is a solution containing 0.1 to 200 mg/ml of an AST-3424 active pharmaceutical ingredient, wherein the solvent of the solution contains a C2-C8 monohydric alcohol.

Furthermore, the solvent of the solution is a liquid solvent containing a solvent mixed by the C2-C8 monohydric alcohol and a C2-C8 dihydric alcohol or trihydric alcohol.

Obviously, in order to further enhance the stability over time and thermal stability, other harmless substances that do not react with the AST-3424 active pharmaceutical ingredient may be added. These substances generally include those below.

Protective gases. The injection is vacuumed to significantly reduce the content of active gases such as $O_2$ and $CO_2$ in the injection, and then charged with an inert gas, such as $N_2$ or other inert gases, that does not react with the active pharmaceutical ingredient, monohydric alcohol, dihydric alcohol, or trihydric alcohol. The protective gas(es) will be dissolved in the injection.

Antioxidants. An appropriate amount of antioxidant (such as vitamin E, vitamin C, or glutathione) is added to the injection to further improve the stability.

In order to improve the compliance of the patients, drugs having anesthetic or analgesic effects may be further added in allowable doses prescribed in the pharmacopoeia or formulary accordingly.

The injection disclosed in the present disclosure may also contain an additional therapeutic agent to form a compound preparation, which exhibits synergistic effects to enhance the therapeutic effects. In particular, it is recommended that these drugs are those regulating the expression level of the AKR1C3 enzyme or the corresponding gene.

In some situations, in order to accommodate special environments, the injection disclosed in the present disclosure may also be added with an antibacterial or antifungal agent.

In addition, substances such as electrolytes (such as salts including NaCl and KCl), glucose and amino acids that are frequently used in the injection to regulate the hydro-salinity balance, the electrolyte balance, the acid-base balance, and the osmotic pressure may also be added as appropriate.

The pH-adjusting substance includes alkali metal salts or alkaline earth metal salts of weak acids such as carbonic acid, phosphoric acid, citric acid, and acetic acid, and inorganic bases such as hydroxides of alkali metals or alkaline earth metals such as Na and K, for example, sodium citrate, potassium citrate, sodium acetate, potassium acetate, potassium dihydrogen phosphate, sodium dihydrogen phosphate, dipotassium hydrogen phosphate, disodium hydrogen phosphate, potassium phosphate, sodium phosphate, sodium hydroxide, potassium hydroxide, sodium bicarbonate, potassium bicarbonate, sodium carbonate, and potassium carbonate. Some examples disclosed in the present disclosure make it clear that some organic amine-based organic bases will cause the injections to be unstable. Although the mechanism of instability is still unknown, such test results provide the guidance or enlightenment that it is not suitable to add organic amine-based organic bases, for example, organic amines such as triethylamine and triethanolamine, without conducting a strict stability test.

Apparently, the above-mentioned protective gases, antioxidants, drugs with anesthetic or analgesic effects, antibacterial agents, antifungal agents and the like are added in very small amounts, which exerts no influence on the properties such as solubility of the AST-3424 active pharmaceutical ingredient or is able to improve the stability, while the additional therapeutic agent, the substances for regulating the hydro-salinity balance, the electrolyte balance, the acid-base balance, and the osmotic pressure, and the pH-adjusting substance need to be added according to actual situations, e.g., purposes, prescribed amount, description in pharmacopoeia and formulary.

The C2-C8 monohydric alcohols include linear, branched or cyclic aliphatic alcohols and aromatic alcohols (excluding phenols and highly active benzyl alcohol).

The C2-C8 dihydric alcohols or trihydric alcohols include linear, branched or cyclic aliphatic alcohols or aromatic alcohols (excluding phenols and highly active benzyl alcohol).

Evidently, the mixed solvent of the C2-C8 monohydric alcohol and the C2-C8 dihydric alcohol or trihydric alcohol as set forth in the present disclosure indicates that the above-mentioned monohydric alcohol and dihydric alcohol or trihydric alcohol should be liquid at normal temperature and normal pressure respectively, or that the mixed solvent is liquid. The polyhydric alcohol is preferably ethylene glycol, propylene glycol, glycerol, mannitol, sorbitol, or a mixture thereof.

Furthermore, the solvent of the solution is a liquid or semi-liquid mixture containing a mixture of the C2-C8 monohydric alcohol and a pharmaceutically suitable water-soluble polymer.

In pharmaceutical preparations, the liquid or semi-liquid mixture obtained by mixing the pharmaceutically suitable water-soluble polymers includes a great variety of polymers such as polyethylene glycol, polyvinyl alcohol, polyvinylpyrrolidone, poloxamer, polysorbate, or glucan.

The monohydric alcohol (preferably ethanol) contained in the injection preparation provided by the present disclosure is used mainly to dissolve and dilute the viscous oily AST-3424 active pharmaceutical ingredient (at the time of synthesis, the monohydric alcohol such as ethanol has been validated to exhibit good solubility for the active pharmaceutical ingredient, but experiments have proved that the stability of the ethanol solution is relatively poor).

The stability of the solution of a single monohydric alcohol such as ethanol is poor. It is speculated that the concentration of the solution changes as a result of volatilization; or the solvent (i.e., ethanol molecule) are so active that the motion of the molecules of the active pharmaceutical ingredient is unhindered and the molecules change rapidly, such that the stability is poor.

After added to the monohydric alcohol, the dihydric alcohol or trihydric alcohol, the water-soluble polymer, and the like make the solution become viscous and exert a thickening effect. At the same time, these substances added will also hinder the motion of the molecules of the active pharmaceutical ingredient and enhance the stability.

Furthermore, the solvent of the stable AST-3424 injection is a mixture of a C2-C4 monohydric alcohol and a C2-C3 dihydric alcohol, and more preferably a mixture of ethanol and propylene glycol.

Furthermore, the monohydric alcohol is not less than 50% by volume in a mixed solvent of the stable AST-3424 injection.

Preferably, the mixed solvent of the stable AST-3424 injection is composed of 75% ethanol and 25% propylene glycol by volume.

In view of many factors such as stability and ease of use, the stable AST-3424 injection disclosed in the present disclosure is a solution containing 10 mg/ml of the AST-3424 active pharmaceutical ingredient. This concentration is the value recommended by the R & D team, and shows better properties in the comparison of experiments.

Furthermore, the stable AST-3424 injection disclosed herein is not added with water, and the water content is controlled within 0.5% by mass.

Evidently, no addition of water means that no water is additionally added in the preparation process, and the other reagents, solvents, and the like used are anhydrous reagents such as anhydrous ethanol and anhydrous propylene glycol. In other words, the water content is required to be controlled during the preparation process of the injection of the present disclosure. In theory, the lower the water content of the injection, the better the stability. In view of the technical difficulties and the realization of industrial mass production, the R & D team considers it better that the water content (determined by the Karl Fischer method) is within 0.5% by mass.

Provided is a stable AST-3424 injection, which is composed of 0.75 ml of anhydrous ethanol, 0.25 ml of anhydrous propylene glycol, and 10 mg of an AST-3424 active pharmaceutical ingredient.

The above-mentioned 1.0-ml injection containing 10 mg of the AST-3424 active pharmaceutical ingredient is a specific example. The injection is filled into a 2 ml- (or 5 ml-) injection vial made of a neutral borosilicate glass tube (brown). Thereafter, the injection vial is filled with inert protective gas, capped with a rubber plug, and sealed with an aluminum-plastic composite cap for antibiotic vial.

It is evident that after 0.75 ml of anhydrous ethanol as mentioned above is mixed with 0.25 ml of anhydrous propylene glycol, the volume will change (having proved to decrease). Therefore, a reasonable volume change is also known to a person skilled in the art (researchers engaged in the fields of pharmaceutical research and development, organic synthesis, preparation research and development, and the like, or medical staff).

In particular, the concentration of the AST-3424 active pharmaceutical ingredient in the injection of this example will be calibrated to 10 mg/ml. Similarly, in the criteria for pharmaceuticals, the actually measured content may also change, and a concentration is considered to be qualified as long as it is within the corresponding range prescribed by the pharmacopoeia or formulary or criteria for pharmaceuticals. In other words, the concentration within the above-mentioned corresponding range is technically equivalent to the calibrated concentration (10 mg/ml).

Provided is a stable AST-3424 injection preparation product, comprising a packaging container and the AST-3424 injection preparation as described above contained in the packaging container, wherein the product contains the AST-3424 active pharmaceutical ingredient in an amount of from 1 to 200 mg, preferably 10 mg or 20 mg, and is filled in a lightproof glass vial made of a neutral borosilicate glass material and charged with protective gas.

Provided is a stable AST-3424 injection preparation product, which is substantially composed of 0.75 ml of anhydrous ethanol, 0.25 ml of anhydrous propylene glycol and 10 mg of an AST-3424 active pharmaceutical ingredient, and is filled in a 2-, 5-, or 10-ml lightproof glass vial made of a neutral borosilicate glass material and charged with protective gas.

Provided is a method for preparing a stable AST-3424 injection, comprising the following steps:

subjecting an AST-3424 active pharmaceutical ingredient and a partial prescription volume of ethanol to a first dissolution and formulation;

adding propylene glycol in a prescription volume for a second dissolution and formulation; and adding the remaining prescription volume of ethanol for mixing and dissolving to obtain a solution containing 0.1 to 200 mg/ml or 1 to 200 mg/ml of the AST-3424 active pharmaceutical ingredient.

In the above preparation method, the AST-3424 active pharmaceutical ingredient and the partial prescription volume of ethanol must be subjected to the first dissolution and formulation to form a concentrated solution, and then propylene glycol and the remaining prescription volume of ethanol are added for dilution.

This operation process is devised based on the property that the AST-3424 active pharmaceutical ingredient is a viscous oily matter. Preferably, the volume of ethanol used for the first dissolution and formulation is 50% of the prescription volume.

Alternatively, the AST-3424 active pharmaceutical ingredient and ethanol are subjected to the first dissolution and formulation; and propylene glycol is added in a prescription volume for the second dissolution and formulation to obtain a solution containing 0.1 to 200 mg/ml or 1 to 200 mg/ml of the AST-3424 active pharmaceutical ingredient.

Further, the present disclosure also discloses an injection for AST-3424 injection, which is a ready-to-use injection of pharmaceutical composition. This composition does not need to be diluted before administration. This composition has already been suitable for administration once produced, and does not require the medical staff to conduct dilution or preparation prior to use.

Obviously, the injection for AST-3424 injection may be a ready-to-use injection for various administration routes, e.g., intradermal, subcutaneous, intramuscular, and intravenous injection.

The present disclosure discloses an injection for AST-3424 injection, wherein a solvent is water, solutes are composed of an AST-3424 active pharmaceutical ingredient, an isotonic regulator, ethanol, propylene glycol, and a pH regulator, the AST-3424 active pharmaceutical ingredient of the injection has a concentration of from 0.001 to 1.000 mg/ml, and the injection has a pH of from 6.8 to 10.5, and is an isotonic solution.

For the injections for injection in the present disclosure, the isotonic regulator may be any medically acceptable isotonic regulator. A suitable isotonic regulator includes, but is not limited to, anhydrous or hydrous sodium chloride, glucose, sucrose, fructose, xylitol, glycerol, sorbitol, mannitol, potassium chloride, mannose, calcium chloride, magnesium chloride, and other inorganic salts, or a mixture thereof.

A solution with a concentration of 308 mmol/L is generally considered to be an isotonic solution for humans, such as 0.9% normal saline and 5% glucose solution. Of course, a solution having a concentration as broad as between 280 and 320 mmol/L is also recognized as an isotonic solution.

Of course, if the objects applicable to be treated are other animals, such as other primates, the concentration of the isotonic solution should be adjusted accordingly.

Furthermore, provided is an injection for AST-3424 injection, wherein the AST-3424 active pharmaceutical ingredient of the injection has a concentration of from 0.004 to 0.94 mg/ml.

Preferably, provided is an injection for AST-3424 intravenous injection, wherein the injection has a pH of from 7.4 to 10.5. The injection for intravenous injection with a pH in the above pH range is more stable, and can ensure storage for a certain period of time (for example, after the injection has been formulated immediately before use, the patient cannot receive injection on time temporarily).

An injection for AST-3424 injection is provided in the present disclosure, wherein the pH regulator is one of sodium citrate, sodium acetate, potassium acetate, potassium dihydrogen phosphate, sodium dihydrogen phosphate, dipotassium hydrogen phosphate, disodium hydrogen phosphate, potassium phosphate, sodium phosphate, sodium hydroxide, potassium hydroxide, sodium bicarbonate, potassium bicarbonate, sodium carbonate, and potassium carbonate, or a mixture thereof.

Provided is an injection for AST-3424 intravenous injection, wherein a solvent is water, solutes are composed of an AST-3424 active pharmaceutical ingredient, glucose, ethanol, propylene glycol, and sodium bicarbonate as a pH regulator, the AST-3424 active pharmaceutical ingredient of the injection has a concentration of from 0.004 to 0.94 mg/ml, the injection has a pH of 7.4, the glucose content is from 4.5 to 5.0% by mass in the injection, and is the injection is an isotonic solution.

Provided is a method for formulating a stable AST-3424 injection into an injection for intravenous injection, comprising: adding an appropriate amount of sodium bicarbonate solution as a pH regulator to a 5% glucose injection, such that the pH value of the mixed solution is 7.4; and adding the stable AST-3424 injection as described above to the above mixed solution for mixing and dissolving, thereby producing the injection for intravenous injection.

During the above dilution and formulation process, the amount and concentration of the sodium bicarbonate solution as the pH regulator, the amount of the 5% glucose injection, and the amount of the AST-3424 injection are obtained by calculation.

BRIEF DESCRIPTION OF THE DRAWINGS

FIG. 1 is a flow chart of the production process for the AST-3424 pharmaceutical preparation.

DETAILED DESCRIPTION

One example provided in the present disclosure is a non-ready-to-use concentrated injection.

The storage-stable concentrated AST-3424 injection disclosed in the present disclosure is a concentrated injection of a pharmaceutical composition. The composition needs to be diluted before administration, and needs to be diluted or prepared as required, when in use, by medical staff or pharmacists or staff in pharmacies or factories.

The concentrated injection of the present disclosure may be diluted by a solution formulated by any medically acceptable isotonic regulator (as a solute) and water for injection (as a solvent).

A suitable isotonic regulator includes, but is not limited to, anhydrous or hydrous sodium chloride, glucose, sucrose, fructose, xylitol, glycerol, sorbitol, mannitol, potassium chloride, mannose, calcium chloride, magnesium chloride, and other inorganic salts. Preferably, the isotonic regulator is glucose or sodium chloride.

The stable AST-3424 injection is a solution containing 1 to 200 mg/ml of the AST-3424 active pharmaceutical ingredient. The solvent of the solution is a mixed solvent of a C2-C8 monohydric alcohol and a C2-C8 dihydric alcohol or trihydric alcohol.

Obviously, in order to further enhance the stability over time and thermal stability, other harmless substances that do not react with the AST-3424 active pharmaceutical ingredient may be added. These substances generally include those below.

Protective gases. The injection is vacuumed to significantly reduce the content of active gases such as $O_2$ and $CO_2$ in the injection, and then charged with an inert gas, such as $N_2$ or other inert gases, that does not react with the active pharmaceutical ingredient, monohydric alcohol, is dihydric alcohol, or trihydric alcohol. The protective gas(es) will be dissolved in the injection.

Antioxidants. An appropriate amount of antioxidant (such as vitamin E, vitamin C, or glutathione) is added to the injection to further improve the stability.

In order to improve the compliance of the patients, drugs having anesthetic or analgesic effects may be further added in allowable doses prescribed in the pharmacopoeia or formulary accordingly.

The injection disclosed in the present disclosure may also contain an additional therapeutic agent to form a compound preparation, which exhibits synergistic effects to enhance the therapeutic effects. In particular, it is recommended that these drugs are those regulating the expression level of the AKR1C3 enzyme or the corresponding gene.

In some situations, in order to accommodate special environments, the injection disclosed in the present disclosure may also be added with an antibacterial or antifungal agent.

In addition, substances such as electrolytes (such as salts including NaCl and KCl), glucose and amino acids that are frequently used in the injection to regulate the hydro-salinity balance, the electrolyte balance, the acid-base balance, and the osmotic pressure may also be added as appropriate.

The pH-adjusting substance includes alkali metal salts or alkaline earth metal salts of weak acids such as carbonic acid, phosphoric acid, citric acid, and acetic acid, and inorganic bases such as hydroxides of alkali metals or alkaline earth metals such as Na and K. Some examples disclosed in the present disclosure make it clear that some organic amine-based organic bases will cause the injections to be unstable. Although the mechanism of instability is still unknown, such test results provide the guidance or enlightenment that it is not suitable to add organic amine-based organic bases, for example, organic amines such as triethylamine and triethanolamine, without conducting a strict stability test.

Apparently, the above-mentioned protective gases, antioxidants, drugs with anesthetic or analgesic effects, antibacterial agents, antifungal agents and the like are added in very small amounts, which exerts no influence on the properties such as solubility of the AST-3424 active pharmaceutical ingredient or is able to improve the stability, while the additional therapeutic agent, the substances for regulating the hydro-salinity balance, the electrolyte balance, the acid-base balance, and the osmotic pressure, and the pH-adjusting substance need to be added according to actual situations, e.g., purposes, prescribed amount, description in pharmacopoeia and formulary.

The C2-C8 monohydric alcohols include linear, branched or cyclic aliphatic alcohols and aromatic alcohols (excluding phenols and highly active benzyl alcohol).

The C2-C8 dihydric alcohols or trihydric alcohols include linear, branched or cyclic aliphatic alcohols and aromatic alcohols (excluding phenols and highly active benzyl alcohol).

Evidently, the mixed solvent of the C2-C8 monohydric alcohol and the C2-C8 dihydric alcohol or trihydric alcohol as set forth in the present disclosure indicates that the above-mentioned monohydric alcohol and dihydric alcohol or trihydric alcohol should be liquid at normal temperature and normal pressure respectively, or that the mixed solvent is liquid.

Apparently, it is also possible that the solvent of the solution is a liquid or semi-liquid mixture containing a mixture of a C2-C8 monohydric alcohol and a pharmaceutically suitable water-soluble polymer. Hereinafter, anhydrous ethanol and anhydrous propylene glycol are taken as examples for illustration.

In view of many factors such as stability and ease of use, the stable AST-3424 injection disclosed in the present disclosure is a solution containing 10 mg/ml of the AST-3424 active pharmaceutical ingredient. This concentration is the value recommended by the R & D team, and shows better properties in the comparison of experiments.

Furthermore, the stable AST-3424 injection disclosed herein is not added with water, and the water content is controlled within 0.5% by mass.

Evidently, no addition of water means that no water is additionally added in the preparation process, and the other reagents, solvents and the like used are anhydrous reagents such as anhydrous ethanol and anhydrous propylene glycol. In other words, the water content is required to be controlled during the preparation process of the injection of the present disclosure. In theory, the lower the water content of the injection, the better the stability. In view of the technical difficulties and the realization of industrial mass production, the R & D team considers it better that the water content (determined by the Karl Fischer method) is within 0.5% by mass.

The stable AST-3424 injection is composed of 0.75 ml of anhydrous ethanol, 0.25 ml of anhydrous propylene glycol, and 10 mg of an AST-3424 active pharmaceutical ingredient.

The above-mentioned 1.0-ml injection containing 10 mg of the AST-3424 active pharmaceutical ingredient represents a specific example. The injection is filled into a 2-ml (or 5-ml) injection vial made of a neutral borosilicate glass tube (brown). Thereafter, the injection vial is filled with inert protective gas, capped with a rubber plug, and sealed with an aluminum-plastic composite cap for antibiotic vial.

It is evident that after 0.75 ml of anhydrous ethanol as mentioned above is mixed with 0.25 ml of anhydrous propylene glycol, the volume will change (having proved to decrease). Therefore, a reasonable volume change is also known to a person skilled in the art (researchers engaged in the fields of pharmaceutical research and development, organic synthesis, preparation research and development, and the like, or medical staff).

In particular, the concentration of the AST-3424 active pharmaceutical ingredient in the injection of this example will be calibrated to 10 mg/ml. Similarly, in the criteria for pharmaceuticals, the actually measured content may also change, and a concentration is considered to be qualified as long as it is within the corresponding range prescribed by the pharmacopoeia or formulary or criteria for pharmaceuticals. In other words, the concentration within the above-mentioned corresponding range is technically equivalent to the calibrated concentration (10 mg/ml).

The excipients used in the present disclosure include a solubilizer, an antioxidant (such as vitamin E, vitamin C, or glutathione), a buffer, a salt, glucose, a stabilizer, and an electrolyte.

The excipients used in the present disclosure include an additional therapeutic agent, an alkalizing agent, an antibacterial agent, an antifungal agent, and a combination thereof.

The product of the present disclosure meets the requirements for the storage-stable mixed AST-3424 injection. The mixed injection is a commercial concentrated product.

In some examples, the concentrated injection provided in the present disclosure still has a content of 90% or more after being stored for 6 months under an accelerated test at ambient temperature (25±2° C., dark brown penicillin vial, humidity: 60±5% RH).

In some examples, the concentrated injection provided in the present disclosure still has a content of 95% or more after being stored for 6 months under an accelerated test at ambient temperature (5±2° C., dark brown penicillin vial, humidity: 60±5% RH).

In some examples, the concentrated injection provided in the present disclosure still has a content of 98% or more after being stored for 6 months under an accelerated test at ambient temperature (−20±2° C., dark brown penicillin vial, humidity: 60±5% RH).

Furthermore, since the AST-3424 active pharmaceutical ingredient is an S-configuration drug, its stability not only depends on the stability of the compound, but also depends on whether it undergoes chiral inversion during storage (investigating the enantiomeric excess EE). In the relatively stable concentrated injections obtained by investigations, the following results are obtained.

In some examples, the concentrated injection provided in the present disclosure still has an EE value of 97% or greater after being stored for 6 months under an accelerated test at ambient temperature (25±2° C., dark brown penicillin vial, humidity: 60±5% RH).

In some examples, the concentrated injection provided in the present disclosure still has an EE value of 97% or greater after being stored for 6 months under an accelerated test at ambient temperature (5±2° C., dark brown penicillin vial, humidity: 60±5% RH).

In some examples, the concentrated injection provided in the present disclosure still has an EE value of 97% or greater after being stored for 6 months under an accelerated test at ambient temperature (−20±2° C., dark brown penicillin vial, humidity: 60±5% RH).

In particular, in some examples, since the concentrated injection is added with an organic amine (triethanolamine), the injection is observed to be less stable than the injection devoid of the organic amine (triethanolamine) with lower content, more impurities, and occurrence of new impurities.

The pH value of the composition of the present disclosure may be adjusted with an appropriate amount of a pH regulator containing acidic or basic groups. A suitable pH regulator generally includes at least an acid or a salt thereof, or includes at least a base or a salt thereof. Acid or base is added for adjustment to achieve the desired pH value. For example, if the pH value is lower than the desired pH value, a base (or some salts) will be added to raise the pH value to the desired pH value.

The amino acids usable in the present disclosure include, for example, arginine, glycine, methionine, or lysine, or a mixture thereof, or a salt thereof, or a mixture of these amino acid and a salt thereof. In some examples, the amino acid has at least one basic group with a pKa value of greater than 5, 6, 7, 8, or 8.5. The amount of the amino acid used in the present disclosure is from 0.1 to 100 mg/mL, from 1 to 50 mg/mL, or from 5 to 25 mg/mL.

In some examples, the concentrated injection of the present disclosure is sterile, for example, is sterilized by a terminal.

The composition injection of the present disclosure is packaged in a medically acceptable packaging container. The packaging container may be an intravenous infusion bag or bottle. The infusion bags and bottles may be made of glass, suitable plastics, or polymer materials. The entirety or most part of the packaging container may comprise the following materials: polyvinyl chloride, polyolefin, polyester, polypropylene, or a combination thereof. In other examples, only the surface material in contact with the pharmaceutical injection contains these materials. In the present disclosure, a penicillin vial is preferred.

The injection provided herein is surrounded by a sheath (such as foil or paper) to prevent the active material from being irradiated by light. In other examples, nitrogen gas is charged between the packaging bag of the injection and the sheath to prevent the composition from being oxidized. In other examples, the packaging container (such as glass or plastics) may be light resistant.

The concentrated injection of the present disclosure may further comprise a certain amount of opioid analgesics.

The opioid analgesics may be selected from drugs such as Alfentanil, Allylrotidine, Alphaprodine, Anileridine, Apomorphine, Apocodeine, Benzmorphine, Bezitramide, Brifentanil, Buprenorphine, Butorphanol, Carfentanil, Dextromoramide, Codeine, Cyclopolychlorinated is Biphenyl s, Cyprenorphine, Desomorphine, Dezocine, Diampromide, Dihydrocodeine, Dimenoxadol, Dimepheptanol, Dimethylthiambutene, Dioxophenylbutyric Acid, Dipipanone, Eptazocine, Ethylmethylthiambutene, Ethylmorphine, Etonitazene, Fentanyl, Heroin, Hydrocodone, Hydroxymethylmorphine, hydromorphone, Ketobemidone, Isomethadone, Levallorphan, Levorphanol, Levophenacylmorphan, Lofentanil, Demerol, Meptazinol, Metazocine, Methadone, Methylmorphine, Metopon, Mirfentanil, Morphine, Morphin-6-Glucuronic acid, Myrophine, Nalbuphine, Papaverine, Nicorandil, Norlevorphanol, Normethadone, Nalorphine, Orphanin/Orphanin FQ (N/OFQ), Normorphine, Norpipanone, Ohmefentanyl, Opium, Oxycodone, Oxydihydromorphinone, Papaveretum, Pentazocine, Phenadoxone, Phenomorphan, Phenazocine, Phenoperidine, Oxyhydromorphinone, Piminodine, Piritramide, Proheptazine, Promedol, Profadol, Properidine, Propiram, Propoxyphene, Remifentanil, Sufentanil, Tapentadol, Tramadol, Trefentanil, Tilidine, and Nalbuphine; any opioid that has an agonistic activity on opioid receptors and belongs to phenanthrene, morphinan, phenylmorphines, methadone, phenylpiperidine, propionanilide-4-anilinopiperidine, 4-arylpiperidine, and 4-isoarylpiperidine; any opioid that has an agonistic activity on opioid receptors and has the same pentacyclic skeleton as Nalmefene, Naltrexone, Buprenorphine, Levorphanol, Meptazinol, Pentazocine, and Dezocine; any analog of fentanyl, a prodrug, a derivative or a medically acceptable salt thereof, or a mixture of racemate or enantiomer thereof that is active on opioid receptors.

The examples below are provided to help with the understanding of the present disclosure, but should not be construed as limitations on the present disclosure. For those of ordinary skill in the art, according to the idea of the present disclosure, there will be changes in the specific embodiments and the scope of application. The content of the present specification should not be construed as a limitation on the present disclosure. Any change made in accordance with the design idea of the present disclosure will be within the scope of protection of the present disclosure.

The specific tests and Examples of the present disclosure are described below.

The following tests reveal some physical and chemical properties of AST-3424 developed by the applicant, which are related to the stability of the concentrated injection and the ready-to-use injection of the present disclosure. The applicant hereby declares that the rights of the following experimental data belongs to the applicant.

I. Studies on Solubility and Solution Stability of AST-3424

1.1 Preparation of Buffer/Solution

As long as the target concentration did not change, a stock solution and a buffer with volumes different from the specified volumes could be used.

Sodium hydroxide solution, 0.2 mol/L: 8.00 g of sodium hydroxide [NaOH] was weighed and dissolved by adding water, and the resulting solution was diluted to 1000 ml by adding water.

Potassium dihydrogen phosphate solution, 0.2 mol/L: 27.22 g of potassium dihydrogen phosphate [$KH_2PO_4$] was weighed and dissolved by adding water, and the resulting solution was diluted to 1000 ml by adding water.

Acetic acid, 2 mol/L: 114.4 ml of acetic acid was measured, diluted to 1000 ml by adding water, and mixed evenly.

Solution of boric acid and potassium chloride, 0.2 mol/L: 12.37 g of boric acid [$H_3BO_3$] and 14.91 g of potassium chloride (KCl) were weighed and dissolved by adding water, and the resulting solution was diluted to 1000 ml by adding water.

pH4.5 acetate buffer: 2.99 g of sodium acetate $NaC_2H_3O_2 \cdot 3H_2O$ was weighed and put in a 1000-ml volumetric flask, to which 14.0 ml of the acetic acid solution was added, and then water was added to the scale, followed by mixing.

pH6.8 phosphate buffer: 50 ml of the potassium dihydrogen phosphate solution was charged in a 200-ml volumetric flask, to which 22.4 ml of the sodium hydroxide solution was added, followed by adding water to the scale.

pH7.4 phosphate buffer: 50 ml of the potassium dihydrogen phosphate solution was measured and charged in a 200-ml volumetric flask, to which 39.1 ml of the sodium hydroxide solution was added, followed by adding water to the scale.

pH10.0 alkaline borate buffer: 50 ml of the solution of boric acid and potassium chloride was measured and charged in a 200-ml volumetric flask, to which 43.7 ml of the sodium hydroxide solution was added, followed by adding water to the scale.

1.2 Solubility Test

An appropriate amount of AST-3424 (hereinafter referred to as the active pharmaceutical ingredient or API) was measured, and put in a suitable container containing 40 ml of the above solution (20 ml for an organic solvent) until there were excessive AST-3424 oil droplets in the solution.

The samples were placed in a constant-temperature shaking incubator, the temperature of which was maintained at 25° C. The samples were shaken at an appropriate speed (100 rpm). Sampling was carried out at each predetermined time point as listed in Table 1, and the pH was examined. Then, the samples were centrifuged (10000 rpm, 10 min), and diluted to a concentration suitable for HPLC analysis (note: accurately recording the dilution ratio after the test) by adding the corresponding solution or organic solvent (dissolving API for solubility study), so as to obtain solubility data.

If a significantly reduced solubility was observed, there was no need to test the solubility at 48 h and 72 h.

TABLE 1

| Sampling Time Points and Test Items for Solubility | | | | | | |
|---|---|---|---|---|---|---|
| Solution/Buffer | 1 h | 4 h | 8 h | 24 h | 48 h | 72 h |
| Ethanol | A | A | A | A | A | A |
| Propylene glycol | A | A | A | A | A | A |
| pH 4.5 sodium acetate buffer | A, P | A, P | A, P | A, P | A, P | A, P |
| pH 6.8 phosphate buffer | A, P | A, P | A, P | A, P | A, P | A, P |
| pH 7.4 phosphate buffer | A, P | A, P | A, P | A, P | A, P | A, P |
| pH 10.0 alkaline borate buffer | A, P | A, P | A, P | A, P | A, P | A, P |
| Purified water | A, P | A, P | A, P | A, P | A, P | A, P |

Note:
A = assay, determining the content of AST-3424 in the solution; P = pH.

1.3 Study on Solution Stability

Approximate 107.32 mg of AST-3424 (50% v/v, ethanol) was measured, and put in 50-ml volumetric flasks, to which solvents (organic solvents, buffer solutions, or purified water) were added to the scale, respectively. At each predetermined time point, 1 ml of the sample was measured for HPLC analysis. If API was stable in different pH solutions, the sampling time would be extended, e.g., 5 days or longer. The specific sampling time and test items were listed in Table 2 below.

TABLE 2

| Sample Analysis Time Points for Study on Solution Stability | | | | | | | |
|---|---|---|---|---|---|---|---|
| Solution/Buffer | 0 h | 1 h | 4 h | 8 h | 24 h | 48 h | 72 h |
| Ethanol | A | A | A | A | A | A | A |
| Propylene glycol | A | A | A | A | A | A | A |
| pH 4.5 sodium acetate buffer | A, P | A | A | A | A | A | A, P |
| pH 6.8 phosphate buffer | A, P | A | A | A | A | A | A, P |

TABLE 2-continued

| Sample Analysis Time Points for Study on Solution Stability | | | | | | | |
|---|---|---|---|---|---|---|---|
| Solution/Buffer | 0 h | 1 h | 4 h | 8 h | 24 h | 48 h | 72 h |
| pH 7.4 phosphate buffer | A, P | A | A | A | A | A | A, P |
| pH 10.0 alkaline borate buffer | A, P | A | A | A | A | A | A, P |
| Purified water | A, P | A | A | A | A | A | A, P |

Note:
A = assay, determining the content of AST-3424 in the solution and the HPLC peak purity and total impurities; P = pH.

1.4 Test Method

For samples used for the assay in the solubility study, about 1 ml of the culture medium was measured, then the resultant was centrifuged at 10000 rpm for 10 min, and the clear solution in lower layer was collected for HPLC analysis. For the study on solution stability, the samples could be directly injected into HPLC for analysis.

Content determination by HPLC method: AST-3424 was used as an external standard for quantitation.

UVDAD detector: wavelength: 230 nm. C18 column, column temperature: 25° C.

Mobile Phases:

A: 10 mmol/L ammonium acetate solution obtained by dissolving ammonium acetate in a mixed solvent of 95% water and 5% acetonitrile by volume;

B: 8 mmol/L ammonium acetate solution obtained by dissolving ammonium acetate in a mixed solvent of 95% acetonitrile and 5% water by volume;

Gradient elution was performed.

1.5 Test Results

The data on solution stability of AST-3424 was summarized in Table 3. The results of the solution stability of AST-3424 showed that at room temperature, API was stable for at least 72 h in ethanol, ethanol/propylene glycol=1/1, and pH7.4 and pH10.0 buffer solutions, and was stable for at least 24 h in the pH6.8 solution. API was unstable in the pH4.5 solution and water, particularly in the pH4.5 acetate buffer.

TABLE 3

| Research Results of Solution Stability of AST-3424 in Different Solutions | | | | | | | | |
|---|---|---|---|---|---|---|---|---|
| | Test | Sampling time point | | | | | | |
| Solvent | Items | 0 h | 1 h | 4 h | 8 h | 24 h | 48 h | 72 h |
| Ethanol | Content (mg/mL) | 1.238 | 1.280 | 1.246 | 1.240 | 1.240 | 1.278 | 1.236 |
| | pH value | — | — | — | — | — | — | — |
| Ethanol/propylene glycol (50:50, v/v) | Content (mg/mL) | 1.295 | 1.287 | 1.287 | 1.287 | 1.302 | 1.284 | 1.275 |
| | pH value | — | — | — | — | — | — | — |
| pH 4.5 acetate buffer | Content (mg/mL) | 0.673 | 0.413 | 0.218 | 0.093 | 0.013 | N/A | N/A |
| | pH value | 4.497 | — | — | — | — | — | 4.477 |
| pH 6.8 phosphate buffer | Content (mg/mL) | 1.202 | 1.200 | 1.193 | 1.185 | 1.168 | 1.145 | 1.102 |
| | pH value | 6.815 | — | — | — | — | — | 6.855 |
| pH 7.4 phosphate buffer | Content (mg/mL) | 1.267 | 1.266 | 1.266 | 1.262 | 1.262 | 1.249 | 1.228 |
| | pH value | 7.481 | — | — | — | — | — | 7.534 |

TABLE 3-continued

Research Results of Solution Stability of AST-3424 in Different Solutions

| Solvent | Test Items | 0 h | 1 h | 4 h | 8 h | 24 h | 48 h | 72 h |
|---|---|---|---|---|---|---|---|---|
| pH 10.0 (alkaline borate buffer) | Content (mg/mL) | 1.265 | 1.265 | 1.261 | 1.258 | 1.261 | 1.257 | 1.242 |
| | pH value | 9.984 | — | — | — | — | — | 10.023 |
| Purified water | Content (mg/mL) | 1.186 | 1.126 | 1.056 | 1.005 | 0.918 | 0.860 | 0.810 |
| | pH value | 5.152 | — | — | — | — | — | 6.435 |

According to the results of solution stability, AST-3424 was very unstable in the pH4.5 acetate buffer. Therefore, the solubility was tested in the pH6.8 phosphate buffer, the pH7.4 phosphate buffer, the pH10.0 alkaline borate buffer, and the purified water. An appropriate amount of AST-3424 was weighed and put into 40 mL of medium (ethanol/propylene glycol: 8 mL, 50:50V/V) until there were excessive floccules in the solution. If the solubility of API in the aqueous solution was greater than 2% (20 mg/ml), there was no need to add more API.

TABLE 4

Research Results of Solubility of AST-3424

| Buffer Salt/Solution | Initial pH value of solution | 1 h pH value | 1 h Content (mg/mL) | 4 h pH value | 4 h Content (mg/mL) | 8 h pH value | 8 h Content (mg/mL) | 24 h pH value | 24 h Content (mg/mL) | 48 h pH value | 48 h Content (mg/mL) |
|---|---|---|---|---|---|---|---|---|---|---|---|
| Ethanol/propylene glycol (50:50, v/v) | — | — | 271.28 | — | 302.33 | — | 301.33 | — | 298.85 | — | 273.84 |
| pH 6.8 (phosphate buffer) | 6.817 | 6.856 | 23.01 | 6.837 | 22.92 | 6.855 | 23.03 | 6.841 | 22.59 | 6.860 | 22.06 |
| pH 7.4 (phosphate buffer) | 7.455 | 7.477 | 23.65 | 7.462 | 23.47 | 7.475 | 23.56 | 7.455 | 23.65 | 7.482 | 23.39 |
| pH 10.0 (alkaline borate buffer) | 10.032 | 9.998 | 23.50 | 9.980 | 23.56 | 9.971 | 23.48 | 9.932 | 23.49 | 9.952 | 23.67 |
| Purified water | 6.169 | 5.004 | 20.92 | 5.651 | 20.12 | 5.971 | 19.68 | 6.378 | 18.83 | 6.512 | 17.79 |

The solubility of AST-3424 was greater than 270 mg/mL in the ethanol/propylene glycol (50:50, v/v) solution. The solubility of API was approximately 23 mg/mL in all of the pH6.8, pH7.4 and pH10.0 solutions, and was approximately 20 mg/mL in water. Since API was unstable in the pH6.8 solution and water, the solubility gradually decreased with time. At different time points, the pH of the solutions of API in pH6.8, pH7.4, and pH10.0 media remained unchanged. In the aqueous solution containing API, the pH value gradually increased from pH5.004 to pH6.512 within 48 h.

1.6 Summary of Physical and Chemical Properties Related to the Injection

Solubility. The solubility of AST-3424 at 25° C. in different solvents was summarized in Table 5. AST-3424 was freely soluble in alcohol solvents such as ethanol/propylene glycol. In particular, the researchers further conducted initial investigation on other monohydric alcohols such as methanol, propanol, and butanol, and ethylene glycol, propylene glycol, glycerol, 1,3-butanediol, 1,2-butanediol, etc., and found that the active pharmaceutical ingredient exhibited good solubility in all of these solvents.

AST-3424 was sparingly soluble in water, the pH6.8 phosphate buffer, the pH7.4 phosphate buffer, and the pH10.0 alkaline borate buffer.

In addition, AST-3424 was stable in the pH7.4 phosphate buffer, but exhibited relatively poor stability in water and in the pH6.8 phosphate buffer. Therefore, the water content should be minimized during the production and storage of the injections (the inventors assumed that the N-containing three-membered ring structure in AST-3424 might be susceptible to ring-opening in the presence of water, causing hydrolysis and degradation).

TABLE 5

| Solubility of AST-3424 | | |
|---|---|---|
| Description of Terms | Solvents | Solubility (mg/mL) |
| Freely soluble (FS) | Ethanol/propylene glycol (50:50, v/v) | 273.84 |
| Sparingly soluble (SPS) | Water | 17.79 |
| | pH 6.8 (phosphate buffer) | 22.06 |
| | pH 7.4 (phosphate buffer) | 23.39 |
| | pH 10.0 (alkaline borate buffer) | 23.67 |

Optical Rotation

The optical rotation of AST-3424 was $[a]^{24}_{D}=-30.04°$ (c=0.006, EtOH).

II. Formulation Design, Preparation and Stability Study of AST-3424 Injection The formulation design, preparation and stability study of AST-3424 were carried out based on the stable property of AST-3424 under alkaline conditions as revealed by the above-mentioned studies on solubility and solution stability.

2.1 Formulation Design and Preparation

The investigation of the formulation of the AST-3424 pharmaceutical preparation comprised selecting various solvents and preparing different formulations.

From the perspectives such as the toxicity of the substance and the safety and availability of the solvent of the injection, the inventors chose the formulation solvent composed of ethanol, propylene glycol, triethanolamine (organic amine, used for adjusting the pH to make it alkaline), and the like, and prepared different formulations.

Then, the dosages of 10 mg/mL and 200 mg/mL were selected according to the solubility to prepare different formulations for study.

Afterwards, study on stability of these different formulations was carried out at −20° C., 2 to 8° C., and 25° C.

An HPLC method was adopted for monitoring the chemical properties of the product, including the content, related substances, and ee value (enantiomeric excess), so as to determine the optimal formulation of AST-3424.

Different formulation compositions of 10 mg/mL of AST-3424 injection were listed in Table 6 below.

TABLE 6

| Different Formulation Compositions of AST-3424 Injection (10 mg/mL) | | | |
|---|---|---|---|
| | Material | | |
| Formulations | Ethanol (EtOH) | Propylene Glycol (PG) | Triethanolamine (Tris) |
| F1 | 100% | NA | NA |
| F2 | 99.5% | NA | 0.5% |
| F3 | 2% | 98% | NA |
| F4 | 2% | 97.5% | 0.5% |
| F5 | 25% | 75% | NA |
| F6 | 25% | 74.5% | 0.5% |
| F7 | 50% | 50% | NA |
| F8 | 50% | 49.5% | 0.5% |
| F9 | 75% | 25% | NA |
| F10 | 75% | 24.5% | 0.5% |
| F1-1 | 70% | 30% | NA |

Different formulation compositions of 200 mg/mL of AST-3424 injection were listed in Table 7 below.

TABLE 7

| Different Formulation Compositions of AST-3424 Injection (200 mg/mL) | | | |
|---|---|---|---|
| | Material | | |
| Formulations | Ethanol (EtOH) | Propylene Glycol (PG) | Triethanolamine (Tris) |
| F1 | 100% | NA | NA |
| F2 | 99.5% | NA | 0.5% |
| F3 | 50% | 50% | NA |
| F4 | 50% | 49.5% | 0.5% |
| F2-1 | 70% | 30% | NA |

AST-3424 (dissolved in ethanol) was weighed accurately, and put in a suitable volumetric flask, to which different solvents were added to produce solutions having a final API concentration of 10 mg/mL or 200 mg/mL. The different formulation compositions were listed in Tables 3 and 4. One milliliter of the bulk solution was measured and filled into a 6-ml brown penicillin vial. After the penicillin vial was sealed with a rubber plug and an aluminum cap, the pharmaceutical preparations were stored at −20±2° C., 5±2° C., or 25±2° C. with a humidity of 60±5% RH in dark brown penicillin vials for different periods of time. At the predetermined time points, the samples were taken and inspected. The test methods were the same as those for the solubility and solution stability described in Section I above.

2.2 Test Results of Stability

At each predetermined time point, the samples were taken, and the content of the active pharmaceutical ingredient and the related substances (i.e., impurities) in the injections were detected by HPLC, so as to obtain the stability test data on the content and the related substances assayed according to the sampling schedules listed in Tables 8 to 10.

TABLE 8

| Summary of Stability Data of Different Formulations at 25° C. (25 + 2° C.) | | | | | | | | | | | |
|---|---|---|---|---|---|---|---|---|---|---|---|
| | | 0 | | 1 month | | 2 months | | 3 months | | 6 months | |
| Formulations | | Assay % | Impurity % | Assay % | Impurity % | Assay % | Impurity % | Assay % | Impurity % | Assay % | Impurity % |
| AST-3424 | F1 | 98.7 | 1.4 | 99.3 | 2.1 | 94.9 | 2.6 | 94.8 | 3.5 | 93.1 | 7.4 |
| Injection | F2 | 98.6 | 1.4 | 100.2 | 3.6 | 95.0 | 5.6 | 88.8 | 8.0 | 80.1 | 14.9 |
| (10 mg/mL) | F3 | 96.1 | 1.3 | 97.0 | 2.5 | 91.1 | 3.8 | 87.0 | 5.9 | 88.7 | 6.7 |
| | F4 | 96.1 | 1.3 | 98.3 | 8.4 | 78.1 | 17.7 | 64.7 | 24.3 | 40.8 | 41.4 |

TABLE 8-continued

Summary of Stability Data of Different Formulations at 25° C. (25 + 2° C.)

| Formulations | | 0 | | 1 month | | 2 months | | 3 months | | 6 months | |
|---|---|---|---|---|---|---|---|---|---|---|---|
| | | Assay % | Impurity % | Assay % | Impurity % | Assay % | Impurity % | Assay % | Impurity % | Assay % | Impurity % |
| | F5 | 97.9 | 1.3 | 98.6 | 2.4 | 94.8 | 3.6 | 89.3 | 5.8 | 88.0 | 6.1 |
| | F6 | 97.4 | 1.3 | 98.5 | 7.2 | 81.2 | 15.1 | 69.3 | 22.0 | 47.7 | 37.2 |
| | F7 | 98.8 | 1.4 | 100.3 | 2.3 | 93.8 | 3.1 | 89.6 | 4.1 | 89.0 | 6.1 |
| | F8 | 98.7 | 1.3 | 99.5 | 5.9 | 85.4 | 11.7 | 73.3 | 17.6 | 55.8 | 31.8 |
| | F9 | 98.7 | 1.4 | 100.3 | 2.0 | 96.6 | 2.7 | 90.9 | 3.5 | 91.1 | 4.9 |
| | F10 | 98.5 | 1.4 | 100.3 | 4.5 | 88.5 | 8.7 | 78.6 | 12.9 | 68.2 | 24.3 |
| | F1-1 | 100.9 | 1.2 | 100.5 | 1.8 | 95.4 | 2.6 | ND | ND | TBD | TBD |
| AST-3424 | F1 | 98.2 | 1.3 | 101.9 | 1.6 | 99.5 | 1.1 | 92.0 | 2.8 | 91.8 | 4.5 |
| Injection | F2 | 99.8 | 1.3 | 101.7 | 3.6 | 88.9 | 2.9 | 79.5 | 8.2 | 72.4 | 13.2 |
| (200 mg/mL) | F3 | 97.9 | 1.3 | 102.0 | 1.7 | 94.0 | 0.9 | 87.5 | 3.3 | 84.4 | 6.8 |
| | F4 | 97.4 | 1.5 | 100.7 | 9.6 | 73.0 | 5.1 | 62.0 | 18.5 | 47.5 | 21.1 |
| | F2-1 | 101.8 | 0.6 | 99.8 | 1.7 | 94.9 | 2.9 | ND | ND | TBD | TBD |

TABLE 9

Summary of Stability Data of Different Formulations at 5° C. (2 to 8° C.)

| Formulations | | 0 | | 1 month | | 2 months | | 3 months | | 6 months | |
|---|---|---|---|---|---|---|---|---|---|---|---|
| | | Assay % | Impurity % | Assay 0% | Impurity % | Assay % | Impurity % | Assay % | Impurity % | Assay % | Impurity % |
| AST-3424 | F1 | 98.7 | 1.4 | 99.0 | 1.3 | 99.2 | 1.3 | 99.7 | 1.2 | 96.9 | 1.4 |
| Injection | F2 | 98.6 | 1.4 | 100.1 | 1.5 | 99.2 | 1.6 | 97.5 | 1.6 | 98.5 | 2.2 |
| (10 mg/mL) | F3 | 96.1 | 1.3 | 98.5 | 1.2 | 96.6 | 1.5 | 95.1 | 1.4 | 96.9 | 1.5 |
| | F4 | 96.1 | 1.3 | 97.6 | 1.3 | 95.6 | 2.6 | 92.6 | 3.2 | 91.4 | 5.3 |
| | F5 | 97.9 | 1.3 | 99.2 | 1.2 | 97.5 | 1.4 | 95.2 | 19.5* | 96.9 | 1.4 |
| | F6 | 97.4 | 1.3 | 99.2 | 1.8 | 96.4 | 2.2 | 92.7 | 2.8 | 93.0 | 4.4 |
| | F7 | 98.8 | 1.4 | 100.0 | 1.3 | 96.6 | 1.3 | 93.9 | 1.6 | 97.0 | 1.3 |
| | F8 | 98.7 | 1.3 | 99.0 | 1.6 | 96.3 | 1.3 | 93.8 | 2.3 | 95.2 | 3.6 |
| | F9 | 98.7 | 1.4 | 99.1 | 1.3 | 97.8 | 1.3 | 95.0 | 1.9 | 97.9 | 1.3 |
| | F10 | 98.5 | 1.4 | 100.6 | 1.5 | 98.0 | 1.3 | 93.5 | 2.0 | 96.4 | 2.9 |
| | F1-1 | 100.9 | 1.2 | 99.7 | 1.1 | 96.2 | 1.2 | ND | ND | TBD | TBD |
| AST-3424 | F1 | 98.2 | 1.3 | 101.4 | 1.2 | 99.1 | 0.7 | 100.0 | 1.1 | 98.1 | 1.2 |
| Injection | F2 | 99.8 | 1.3 | 100.1 | 1.3 | 98.7 | 0.6 | 97.1 | 1.6 | 102.5 | 2.3 |
| (200 mg/mL) | F3 | 97.9 | 1.3 | 100.0 | 11 | 97.3 | 0.4 | 96.4 | 1.2 | 97.7 | 1.2 |
| | F4 | 97.4 | 1.5 | 99.6 | 1.5 | 95.9 | 0.8 | 92.6 | 2.8 | 88.1 | 6.1 |
| | F2-1 | 101.8 | 0.6 | 101.2 | 1.1 | 97.9 | 1.2 | ND | ND | TBD | TBD |

TABLE 10

Summary of Stability Data of Different Formulations at −20° C. (−22 to −18° C.)

| Formulations | | 0 | | 1 month | | 2 months | | 3 months | | 6 months | |
|---|---|---|---|---|---|---|---|---|---|---|---|
| | | Assay % | Impurity % | Assay % | Impurity % | Assay % | Impurity % | Assay % | Impurity % | Assay % | Impurity % |
| AST-3424 | F1 | 98.7 | 1.4 | 99.3 | 1.1 | 96.4 | 1.2 | 96.0 | 1.1 | 95.9 | 1.2 |
| Injection | F2 | 98.6 | 1.4 | 100.2 | 1.2 | 96.9 | 1.2 | 98.6 | 1.1 | 98.3 | 1.3 |
| (10 mg/mL) | F3 | 96.1 | 1.3 | 97.0 | 1.2 | 95.7 | 1.2 | 99.2 | 1.1 | 98.6 | 1.2 |
| | F4 | 96.1 | 1.3 | 98.3 | 1.3 | 95.3 | 1.3 | 97.6 | 1.1 | 96.4 | 1.6 |
| | F5 | 97.9 | 1.3 | 98.6 | 1.2 | 95.9 | 1.1 | 96.8 | 3.2 | 96.7 | 1.2 |
| | F6 | 97.4 | 1.3 | 98.5 | 1.3 | 96.6 | 1.4 | 98.1 | 1.2 | 96.1 | 1.4 |
| | F7 | 98.8 | 1.4 | 100.3 | 1.2 | 96.8 | 1.2 | 97.3 | 1.5 | 97.5 | 1.1 |
| | F8 | 98.7 | 1.3 | 99.5 | 1.2 | 97.6 | 1.3 | 97.7 | 1.2 | 97.2 | 1.3 |
| | F9 | 98.7 | 1.4 | 100.3 | 1.2 | 98.5 | 1.1 | 98.4 | 1.1 | 98.0 | 1.1 |
| | F10 | 98.5 | 1.4 | 100.3 | 1.3 | 98.7 | 1.2 | 94.0 | 1.1 | 97.9 | 1.3 |
| | F1-1 | 100.9 | 1.2 | 101.9 | 1.1 | 96.4 | 1.1 | ND | ND | TBD | TBD |
| AST-3424 | F1 | 98.2 | 1.3 | 101.9 | 1.1 | 101.3 | 0.8 | 99.2 | 1.1 | 99.9 | 1.1 |
| Injection | F2 | 99.8 | 1.3 | 101.7 | 1.1 | 99.9 | 0.8 | 97.8 | 1.0 | 94.7 | 1.1 |
| (200 mg/mL) | F3 | 97.9 | 1.3 | 102.0 | 1.1 | 98.0 | 0.5 | 97.1 | 0.9 | 97.4 | 1.0 |
| | F4 | 97.4 | 1.5 | 100.7 | 1.1 | 97.6 | 0.5 | 97.2 | 0.9 | 97.9 | 1.2 |
| | F2-1 | 101.8 | 0.6 | 101.9 | 1.0 | 98.0 | 1.2 | ND | ND | TBD | TBD |

The EE values of seven relatively stable formulations were measured and recorded in Table 11 below.

TABLE 11

EE % Value of Relatively Stable Formulations

| Storage | | Sampling time points | | | | |
|---|---|---|---|---|---|---|
| conditions | Formulations | 0 | 1 month | 2 months | 3 months | 6 months |
| 25° C. | F1 (10 mg/mL) | / | 97.86 | 97.85 | 97.89 | 97.86 |
| | F7 (10 mg/mL) | / | 97.85 | 97.85 | 97.91 | 97.89 |
| | F9 (10 mg/mL) | / | 97.85 | 97.84 | 97.90 | 97.87 |
| | F1-1 (10 mg/mL) | 97.84 | 97.91 | / | / | TBD |
| | F1 (200 mg/mL) | / | 97.63 | 97.55 | 97.62 | 97.67 |
| | F3 (200 mg/mL) | / | 97.69 | 97.68 | 97.65 | 97.57 |
| | F2-1 (200 mg/mL) | 97.84 | 97.89 | | / | TBD |
| 2-8° C. | F1 (10 mg/mL) | | 97.85 | 97.84 | 97.92 | 97.94 |
| | F7 (10 mg/mL) | / | 97.84 | 97.84 | 97.93 | 97.94 |
| | F9 (10 mg/mL) | / | 97.85 | 97.84 | 97.93 | 97.89 |
| | F1-1 (10 mg/mL) | 97.84 | 97.94 | / | / | TBD |
| | F1 (200 mg/mL) | / | 97.68 | 97.69 | 97.77 | 97.83 |
| | F3 (200 mg/mL) | | 97.71 | 97.72 | 97.77 | 97.87 |
| | F2-1 (200 mg/mL) | 97.84 | 97.94 | / | / | TBD |
| −20° C. | F1 (10 mg/mL) | / | / | | 97.95 | 97.93 |
| | F7 (10 mg/mL) | / | / | / | 97.95 | 97.92 |
| | F9 (10 mg/mL) | | / | | 97.95 | 97.89 |
| | F1-1 (10 mg/mL) | 97.84 | 97.97 | / | / | TBD |
| | F1 (200 mg/mL) | / | / | / | 97.79 | 97.84 |
| | F3 (200 mg/mL) | / | / | / | 97.81 | 97.85 |
| | F2-1 (200 mg/mL) | 97.84 | 97.97 | / | / | TBD |

Note:
/ denoted “not tested”;
TBD denoted “not detected”;
* denoted that the data is an outlier;
ND denoted “not detected because of below the detection limit of the instrument”; and
N/A denoted "not contained".

2.3 Results and Discussion

The stability results of different formulations of the AST-3424 injection were listed in Tables 8 to 11. The stability results of different formulations stored at 25° C. showed that the stability of the formulation was improved with the increase of the proportion of ethanol in the formulation. The formulations containing triethanolamine was less stable than those devoid of triethanolamine.

At a dose specification of 10 mg/ml, F9 was the most stable formulation among others.

For the formulations stored at 2 to 8° C. and −20° C., the stability of the samples was significantly improved. Compared with the formulations stored at 2 to 8° C., the samples stored at −20° C. were more stable. The enantiomeric excesses (EE) of the stable formulations (i.e., F1 (10 mg/ml), F7 (10 mg/ml), F9 (10 mg/ml), F1-1 (10 mg/ml), F1 (200 mg/ml), F3 (200 mg/ml) and F2-1 (200 mg/ml)) were tested. The EE values of the relatively stable formulations were shown in Table 11. The EE values of all formulations remained unchanged within 6 months under different storage conditions, indicating that isomer conversion did not occur to the active ingredients in these formulations.

The following could be concluded from the comparisons of the stability test results of different formulations.

(1) According to the results of the formulation screening study in the above tables, the stability of the pharmaceutical preparations was improved as the proportion of ethanol in the formulations increased. On the other hand, if triethanolamine was added to the preparations, the pharmaceutical preparations became unstable.

(2) The results of stability study showed that the pharmaceutical preparations were more stable at a storage temperature of −20° C. than at a storage temperature of 2 to 8° C. or 25° C. The storage temperature had significant influence on the stability of pharmaceutical preparations.

(3) Through the concentration screening of the AST-3424 pharmaceutical preparations, the candidate formulation coded as F9 was determined to be the most stable one among the candidate formulations. The six-month stability results showed that the test items of the related substances and the ee values did not change significantly.

(4) According to the investigation results of the formulations, formulation F9 (75.0% ethanol and 25.0% propylene glycol) was selected as the final candidate formulation for the AST-3424 pharmaceutical preparation.

III. Study on Photostability of AST-3424 Injection

3.1 Sample Preparation and Test Results

After the AST-3424 injection (1 mL: 10 mg, Formulation F9) was prepared, it was put in 1.1-mL transparent vials and brown vials respectively, and the vials were sealed. Prior to the photostability study, the light intensity of the stability test chamber was measured to ensure that the total illuminance of the test samples was greater than $1.2\times10^6$ Lux·hrs, and the ending time of the photostability experiment was calculated (the light intensity of the photostability test chamber where the samples were placed was 5200 Lux, and the test period was required to be not less than 10 days). All samples were placed in the photostability test chamber, and sampling was carried out on day 5, day 10 and day 20 to check the appearance, content, and related substances of each sample.

The transparent vials were penicillin vials (pharmaceutical grade) made of neutral borosilicate glass tubes. The brown vials were penicillin vials (pharmaceutical grade) made of neutral borosilicate glass tubes. Upon experiment, considering the influence of acidity or alkalinity, the ingredients and the pH of the neutral borosilicate glass tubes were suitable for the characteristic that the AST-3424 injection of the present disclosure was stable under alkaline conditions.

The initially prepared AST-3424 injection was placed in a brown vial as a test sample for control and stored at −20° C., and the sample was tested together with the samples stored in the photostability test chamber at each sampling time point. The transparent vial wrapped with aluminum foil was used as the control group for the photostability study, and sampling and testing were carried out (using the HPLC method described in Section 1.4) according to the same sampling schedule. The results were shown in Table 12 below.

TABLE 12

Results of Photostability Study on AST-3424 Injection

| Product Name | Test Time | Test Items: Appearance | Content % | Related substances % |
|---|---|---|---|---|
| AST-3424 injection (1 mL:10 mg) stored in transparent vials | Control sample test-1 (5 days) | Yellowish liquid | 97.2 | 1.3 |
| | 5 days | Brown liquid | 79.3 | N/A |
| | Control sample test-2 (10 days) | Yellowish liquid | 100.6 | 1.3 |
| | 10 days | Brown liquid | 72.7 | N/A |
| | Control sample test-3 (20 days) | Yellowish liquid | 99.9 | 1.3 |
| | 20 days | Brown liquid | 56.6 | N/A |
| AST-3424 injection (1 mL:10 mg) stored in brown vials | Control sample test-1 (5 days) | Yellowish liquid | 97.2 | 1.3 |
| | 5 days | Yellowish liquid | 98.3 | 1.3 |
| | Control sample test-2 (10 days) | Yellowish liquid | 100.6 | 1.3 |
| | 10 days | Yellowish liquid | 99.9 | 1.3 |
| | Control sample test-3 (20 days) | Yellowish liquid | 99.9 | 1.3 |
| | 20 days | Yellowish liquid | 97.3 | 1.6 |
| AST-3424 injection (1 mL:10 mg) stored in transparent vials wrapped in aluminum foil | Control sample test-1 (5 days) | Yellowish liquid | 97.2 | 1.3 |
| | 5 days | Yellowish liquid | 98.0 | 1.3 |
| | Control sample test-2 (10 days) | Yellowish liquid | 100.6 | 1.3 |
| | 10 days | Yellowish liquid | 99.7 | 1.3 |
| | Control sample test-3 (20 days) | Yellowish liquid | 99.9 | 1.3 |
| | 20 days | Yellowish liquid | 99.3 | 1.4 |

Note:
content, i.e., the relative percentage content of the corresponding substance tested by HPLC; related substances, i.e., impurities in the active pharmaceutical ingredient API.

3.2 Conclusion

The results of the photostability of the AST-3424 injection stored in a transparent vial indicated that the appearance of the AST-3424 injection changed from yellowish to brown after 5-day light illumination. The content of the active ingredient at each sampling time point decreased. By the end of 20-day light illumination, the content of the active ingredient dropped from 99.9% to 56.6%.

The AST-3424 injection sample stored in a transparent vial wrapped with aluminum foil was exposed to light illumination for 20 days, and the content of the active ingredient and the impurities remained basically unchanged.

The AST-3424 injection stored in a brown vial was exposed to light illumination for 10 days, and the content of the active ingredient and the related substances in the sample remained unchanged, but when the above injection was exposed to light illumination for 20 days, the content of the active ingredient dropped from 99.9% to 97.3%.

The results of photostability study showed that the AST-3424 injection was unstable under illumination conditions and should be stored in an amber (brown) vial to avoid direct light exposure.

IV. Study on Temperature Cycling Stability of AST-3424 Injection

In order to evaluate the stability of the active ingredient AST-3424 in the temperature cycle, the temperature cycling stability of the AST-3424 injection was studied to provide guidance for how to store the product during transportation, storage and use.

Section II described above had specified that the optimal storage temperature for the AST-3424 injection was −20° C. When in use, however, the stored injection had to be taken from a low-temperature environment to a normal-temperature (25° C.) environment, or the injection was returned from the normal-temperature (25° C.) environment to the low-temperature environment with an optimal storage temperature of −20° C. Such shock caused by temperature cycling would possibly affect the stability of the injection. For this reason, there was a need to study the temperature cycling stability of the injection.

4.1 Test Operation

The prepared AST-3424 injection (1 ml: 10 mg) was first stored at −20° C. for 2 days, and the sample was then transferred to an environment with a temperature of 2 to 8° C. and stored for 2 days, which was defined as one temperature cycle. Three temperature cycles were repeated, and the sample was analyzed following each temperature cycle. The initially prepared AST-3424 injection was stored in a refrigerator at −20° C. as control. Test items included the appearance, content, and related substances. The above-mentioned process was repeated to perform a temperature cycle from −20° C. to 25° C.

4.2 Test Results

Two samples (4 vials) were prepared for each temperature cycle. One sample (2 sample vials) was tested, while the other sample (2 sample vials) was used as a spare. The cycling time in the original test record was listed in Table 13. The results of the temperature cycling stability were summarized in Table 14.

TABLE 13

| Sampling Schedule for Temperature Cycling Study | | | | | | |
|---|---|---|---|---|---|---|
| Product Name | Cycle | Stored at −20° C. | Taken from −20° C. | Stored at 2-8° | Taken from 2-8° | Pull |
| AST-3424 injection (1 mL:10 mg) | First cycle | 11 AUG. 2017 (12 vials) | 13 AUG. 2017 (12 vials) | 13 AUG. 2017 (12 vials) | 15 AUG. 2017 (12 vials) | 4 vials |
| | Second cycle | 15 AUG. 2017 (8 vials) | 17 AUG. 2017 (8 vials) | 17 AUG. 2017 (8 vials) | 19 AUG. 2017 (8 vials) | 4 vials |
| | Third cycle | 19 AUG. 2017 (4 vials) | 21 AUG. 2017 (4 vials) | 21 AUG. 2017 (4 vials) | 23 AUG. 2017 (4 vials) | 4 vials |
| | Cycle | Stored at −20° C. | Taken from −20° C. | Stored at 25° C. | Taken from 25° C. | Pull |
| | First cycle | 11 AUG. 2017 (12 vials) | 13 AUG. 2017 (12 vials) | 13 AUG. 2017 (12 vials) | 15 AUG. 2017 (12 vials) | 4 vials |
| | Second cycle | 15 AUG. 2017 (8 vials) | 17 AUG. 2017 (8 vials) | 17 AUG. 2017 (8 vials) | 19 AUG. 2017 (8 vials) | 4 vials |
| | Third cycle | 19 AUG. 2017 (4 vials) | 21 AUG. 2017 (4 vials) | 21 AUG. 2017 (4 vials) | 23 AUG. 2017 (4 vials) | 4 vials |

Vials: the number of drug vials put in certain environments;
Pull: the number of sampling

TABLE 14

| Results of Temperature Cycling Stability of AST-3424 Injection | | | | |
|---|---|---|---|---|
| | | Test Items | | |
| Product Name | | Appearance | Context % | Related substances % |
| AST-3424 injection (1 ml:10 mg) | Test Cycle (−20° C. to 2-8° C.) | | | |
| | Control-1 | Yellowish liquid | 95.9 | 1.3 |
| | First cycle | Yellowish liquid | 97.1 | 1.3 |
| | Control-2 | Yellowish liquid | 98.3 | 1.3 |
| | Second cycle | Yellowish liquid | 97.6 | 1.3 |
| | Control-3 | Yellowish liquid | 98.7 | 1.3 |
| | Third cycle | Yellowish liquid | 100.0 | 1.3 |
| | Test Cycle (−20° C. to 25° C.) | | | |
| | Control-1 | Yellowish liquid | 95.9 | 1.3 |
| | First cycle | Yellowish liquid | 97.6 | 1.3 |
| | Control-2 | Yellowish liquid | 98.3 | 1.3 |
| | Second cycle | Yellowish liquid | 98.2 | 1.4 |
| | Control-3 | Yellowish liquid | 98.7 | 1.3 |
| | Third cycle | Yellowish liquid | 100.5 | 1.4 |

Control: control group;
first cycle, second cycle, third cycle: the first cycle, the second cycle, the third cycle

4.3 Test Results

The results of three temperature cycles (from −20° C. to 2-8° C.) of the AST-3424 injection indicated that the content of the active ingredient and the impurities in the samples remained unchanged during this period. The temperature cycling test results of the AST-3424 injection from −20° C. to 25° C. indicated that the content of the active ingredient in the samples did not change either, and the content of the related substances merely increased slightly (changed from 1.3% to 1.4%). The above results showed that AST-3424 injection was stable in the three temperature cycles from −20° C. to 2-8° C. and the three temperature cycles from −20° C. to 25° C.

V. Preparation Process of Concentrated Injection and Specific Examples

The flow chart of the production process for the AST-3424 pharmaceutical preparation was as shown in FIG. 1.

Step 1: Dissolving and Mixing

Step 2-1: Adding an Ethanol Solution

A prescription amount of the AST-3424 active pharmaceutical ingredient (depyrogenated) was weighed in a beaker, and put into a mixing tank. 50% of the prescription volume of medicinal anhydrous ethanol (depyrogenated) was added and stirred until dissolution (dissolution time: 15 min, stirring speed: 50 HZ, i.e., 50 rpm).

Step 2-2: Adding Propylene Glycol

A prescription volume of the propylene glycol (depyrogenated) was added and stirred until dissolution (dissolution time: 15 min, stirring speed: 50 HZ, i.e., 50 rpm).

Step 2-3: Mixing

50% of the prescription volume of medicinal anhydrous ethanol (depyrogenated) was added and stirred until dissolution (dissolution time: 15 min, stirring speed: 50 HZ, i.e., 50 rpm).

Step 3: Sterilizing

The solution obtained in Step 2 was sterilized.

Step 4: Sterile Filling

Sterile filling was performed with a filling volume of 1.0 to 1.2 ml (0.860 to 1.032 g).

Step 5: Capping and Appearance Inspection

The filled vials were conveyed to the capping room via a conveyor belt and capped. Appearance inspection was carried out.

Step 6: Testing Before Release

The AST-3424 injection was sampled for QC inspection, and after released by QA, the injection was stored at −20° C. for clinical use.

The formulation design, the properties such as stability, and the specific preparation examples of the concentrated injection had been studied above. The preparation process of the ready-to-use injection was disclosed below and the stability study was undertaken.

VI. Compounding and Stability Study of Ready-to-Use Intravenous Injection

In order to provide the information on compatibility of the AST-3424 injection with a compounding solution, it was necessary to investigate the short-term stability of the injection in the commonly used diluent for intravenous preparation, i.e., 5% glucose injection. Considering that the API was unstable in an acidic environment, the pH of 5% glucose injection was first adjusted to 7.4 with a sodium bicarbonate solution.

6.1 Experimental Method and Process

Preparation of 5% Glucose Injection 0.22 mL of sodium bicarbonate solution was added into 5% glucose injection (250 mL:12.5 g) via a 1-mL syringe, and the resultant was mixed well. At this time, the pH of the mixed solution was approximately 7.4.

Preparation of AST-3424 Compound Solution

The AST-3424 injection (1 mL:10 mg, clinical batch number: 20170701) and 5% glucose injection were formulated into compound solutions at concentrations of 0.004 mg/mL, 0.071 mg/mL, and 0.94 mg/mL.

Preparation of 0.004 mg/mL of Compound Solution

An AST-3424 injection (1 mL:10 mg) was taken, from which 0.1 mL of the injection was drawn using a 1-mL syringe and added to a mixing bag containing 250 mL of 5% glucose injection (the pH was adjusted to 7.4 with a pH regulator). Prior to storage and sampling, the mixing bag was overturned several times to ensure that the mixed solution was evenly mixed.

Preparation of 0.071 mg/mL of Compound Solution 1.8 mL of the sample was drawn from two vials filled with the AST-3424 injections via a 2.5-mL syringe and added into a mixing bag containing 250 mL of 5% glucose injection (the pH was adjusted to 7.4 with a pH regulator in advance). Prior to storage and sampling, the mixing bag was overturned several times to ensure that the mixed solution was evenly mixed.

Preparation of 0.94 mg/mL of Compound Solution 26 mL of the sample was drawn from 26 vials filled with the AST-3424 injections via a 30-mL syringe and added into a mixing bag containing 250 mL of 5% glucose injection (the pH was adjusted to 7.4 with a pH regulator in advance). Prior to storage and sampling, the mixing bag was overturned several times to ensure that the mixed solution was evenly mixed.

Temperature and Illumination Conditions

All samples of the compound solutions were placed under natural light conditions and stored at room temperature (25±3° C.) for 24 h.

Sampling Time Points and Test Items

Two 10-mL samples of the compound solution were drawn from each bag by a 20-mL syringe at 0 h, 1 h, 2 h, 4 h, 8 h, and 24 h, respectively. One sample was used for test, and the other sample was used as a spare. The test items were as follows:

1) visual inspection;
2) osmotic pressure (initial and last sampling time points);
3) pH value of the compound solution;
4) content (tested by the test method described in Section 1.4);
5) related substances (tested by the test method described in Section 1.4); and
6) e.e.

TABLE 15

Sampling Time Points and Test Items of AST-3424 Compound Solution

| Sample Concentration | Time Points (h) 0 | 1 | 2 | 4 | 8 | 24 |
|---|---|---|---|---|---|---|
| 0.004 mg/mL | I, O, P, A | I, P, A | I, P, A | I, P, A | I, P, A | I, O, P, A |
| 0.071 mg/mL | I, O, P, A, R, E | I, P, A, R, E | I, P, A, R, E | I, P, A, R, E | I, O, P, A, R, E | I, O, P, A, R, E |
| 0.94 mg/mL | I, O, P, A, R, E | I, P, A, R, E | I, P, A, R, E | I, P, A, R, E | I, O, P, A, R, E | I, O, P, A, R, E |

Note:
I = visual inspection; O = osmotic pressure; P = pH value; A = content; R = related substance; E = e.e. value.

6.2 Experimental Results

All of the experimental data were recorded in Tables 16 to 20, summarizing the stability data of the AST-3424 compound solutions diluted to different concentrations.

TABLE 16

Summary of Stability Data of the Compound Solution of 0.004 mg/mL of AST-3424 Injection (1 mL:10 mg) and 5% glucose injection
Date: 7 MAR. 2018-8 MAR. 2018; temperature: 25.6 to 26.2° C.; relative humidity: 26.8% to 33.8%

| Sampling time points (hr) | Test Items Appearance | Osmotic pressure (mOmsmol/kg) | pH | Content[1] (mg/mL) | Initial value (%) | e.e (%) |
|---|---|---|---|---|---|---|
| 0 | Colorless clear solution | 253 | 7.64 | 0.0055 | Initial | — |
| 1 | Colorless clear solution | — | 7.74 | 0.0055 | 100.0 | — |

TABLE 16-continued

Summary of Stability Data of the Compound Solution of 0.004 mg/mL of AST-3424 Injection (1 mL:10 mg) and 5% glucose injection
Date: 7 MAR. 2018-8 MAR. 2018; temperature: 25.6 to 26.2° C.; relative humidity: 26.8% to 33.8%

| | Test Items | | | | | |
|---|---|---|---|---|---|---|
| Sampling time points (hr) | Appearance | Osmotic pressure (mOmsmol/kg) | pH | Content[1] (mg/mL) | Initial value (%) | e.e (%) |
| 2 | Colorless clear solution | — | 7.74 | 0.0055 | 100.0 | — |
| 4 | Colorless clear solution | — | 7.72 | 0.0055 | 100.0 | — |
| 8 | Colorless clear solution | 255 | 7.76 | 0.0055 | 100.0 | — |
| 24 | Colorless clear solution | 262 | 7.89 | 0.0055 | 100.0 | — |

TABLE 17

Summary of Stability Data of the Compound Solution of 0.071 mg/mL of AST-3424 Injection (1 mL:10 mg) and 5% glucose injection
Date: 8 MAR. 2018-9 MAR. 2018; temperature: 23.9 to 26.6° C.; relative humidity: 18.1% to 28.9%

| | Test Items | | | | | |
|---|---|---|---|---|---|---|
| Sampling time points (hr) | Appearance | Osmotic pressure (mOmsmol/kg) | pH | Content[2] (mg/mL) | Initial value (%) | e.e (%) |
| 0 | Colorless clear solution | 284 | 7.52 | 0.067 | Initial | 97.2 |
| 1 | Colorless clear solution. | — | 7.53 | 0.067 | 100.0 | 97.6 |
| 2 | Colorless clear solution | — | 7.60 | 0.066 | 98.5 | 97.6 |
| 4 | Colorless clear solution | — | 7.52 | 0.066 | 98.5 | 97.6 |
| 8 | Colorless clear solution | 284 | 7.55 | 0.067 | 100.0 | 97.5 |
| 24 | Colorless clear solution | 288 | 7.62 | 0.068 | 101.5 | 97.6 |

TABLE 18

Summary of Data of the Related Substances of the Compound Solution of 0.071 mg/mL of AST-3424 Injection (1 mL:10 mg) and 5% glucose injection

| Sampling time (hr) | 0 | 1 | 2 | 4 | 8 | 24 |
|---|---|---|---|---|---|---|
| Related substances | Number of impurities with a content exceeding 0.05% | Number of impurities with a content exceeding 0.05% | Number of impurities with a content exceeding 0.05% | Number of impurities with a content exceeding 0.05% | Number of impurities with a content exceeding 0.05% | Number of impurities with a content exceeding 0.05% |
| | 3 | 4 | 4 | 4 | 4 | 5 |
| Total content of impurities | 0.5% | 0.6% | 0.6% | 0.6% | 0.6% | 0.9% |

TABLE 19

Summary of Stability Data of the Compound Solution of 0.94 mg/mL of AST-3424 Injection (1 mL:10 mg) and 5% glucose injection
Date: 9 MAR. 2018-10 MAR. 2018; temperature: 22.1 to 27.2° C.; relative humidity: 18.1% to 25.2%

| | Test Items | | | | | |
|---|---|---|---|---|---|---|
| Sampling time points (hr) | Appearance | Osmotic pressure (mOmsmol/kg) | pH | Content[2] (mg/mL) | Initial value (%) | e.e (%) |
| 0 | Yellowish clear solution | 564 | 7.49 | 0.86 | Initial | 97.5 |
| 1 | Yellowish clear solution | — | 7.62 | 0.85 | 98.8 | 97.5 |
| 2 | Yellowish clear solution | — | 7.59 | 0.85 | 98.8 | 97.5 |
| 4 | Yellowish clear solution | — | 7.57 | 0.86 | 100.0 | 97.5 |
| 8 | Yellowish clear solution | 571 | 7.58 | 0.85 | 98.8 | 97.4 |
| 24 | Yellowish clear solution | 561 | 7.47 | 0.85 | 98.8 | 97.4 |

TABLE 20

Summary of Data of the Related Substances of the Compound Solution of 0.94 mg/mL of AST-3424 Injection (1 mL:10 mg) and 5% glucose injection

| Sampling time (hr) | 0 | 1 | 2 | 4 | 8 | 24 |
|---|---|---|---|---|---|---|
| Related substances | Number of impurities with a content exceeding 0.05%<br>5 | Number of impurities with a content exceeding 0.05%<br>5 | Number of impurities with a content exceeding 0.05%<br>5 | Number of impurities with a content exceeding 0.05%<br>6 | Number of impurities with a content exceeding 0.05%<br>6 | Number of impurities with a content exceeding 0.05%<br>7 |
| Total content of impurities | 0.6% | 0.6% | 0.6% | 0.6% | 0.7% | 0.9% |

Remarks

Regarding the Content of the Compound Solution

1) To prepare 0.004 mg/ml compound solution, the volume of the AST-3424 injection should be 0.1 mL, but it was not easy to accurately measure 0.1 mL of the sample with a 1-mL syringe. 0.0055 mg/mL was the result actually measured at the initial time point, and its value was approximately 138% of the theoretical value.
2) The actual volume of 5% glucose injection was approximately 268 mL, but its theoretical volume was 250 mL. Therefore, at the time of formulating samples with concentrations of 0.071 g/mL and 0.94 g/mL, the actual concentrations at the initial time point were 0.067 mg/mL and 0.86 mg/mL, respectively.
3) PRT: retention time, unit: minutes, the corresponding retention time of a chromatographic peak of certain impurity detected by the HPLC method in Section 1.4 corresponded to certain impurity.
4) Initial: initial value.

6.3 Conclusions of Test

1) When stored at room temperature (25±3° C.) for 24 h under natural light conditions, none of the samples showed significantly change. The compound solutions with concentrations of 0.004 mg/mL and 0.071 mg/mL were colorless clear solutions in appearance. The compound solution with a concentration of 0.96 mg/mL was a yellowish clear solution.
2) The osmotic pressure of the compound solution at a low concentration (0.004 mg/mL) was lower than the isotonic pressure, and the solution with a concentration of 0.071 mg/mL (284 to 288 mmol/kg) was almost isotonic (solution with a concentration of 0.074 mg/mL was an isotonic solution). The compound solution at a high concentration (0.94 mg/mL) was hypertonic (561 to 571 mmol/kg). The data of osmotic pressure at the sampling time points (0 h, 8 h and 24 h) showed that the osmotic pressures of the compound solutions at three concentrations remained constant within 24 h.
3) During the 24-hour observation, the pH values of the compound solutions with concentrations of 0.004 mg/mL, 0.071 mg/mL and 0.94 mg/mL fluctuated little during storage.
4) The assay results showed that the compound solutions with concentrations of 0.004 mg/mL, 0.071 mg/mL and 0.94 mg/mL were stable during the 24-hour storage period.
5) In terms of the related substances, the content of the total impurities in the compound solutions with concentrations of 0.071 mg/mL and 0.94 mg/mL did not exceed 2.0% within 24 h, and basically remained unchanged for 8 h at room temperature (25±3° C.). However, the total impurities in the compound solution with a concentration of 0.94 mg/mL increased within 24 h. A new impurity peak with a content ranging from about 0.26% to 0.35% was observed after the compound solutions with concentrations of 0.071 mg/mL and 0.94 mg/mL were stored for 8 h and 4 h, respectively. In addition, a new impurity peak with a content ranging from about 0.10% to 0.13% was observed after the compound solutions with concentrations of 0.071 mg/mL and 0.94 mg/mL were stored for 24 h, respectively. The related substances in the compound solution at low concentration (0.004 mg/mL) were not tested since the AST-3434 content was below the quantitative limit.

6) At two concentrations of 0.071 mg/mL and 0.94 mg/mL, the e.e. values of the compound solutions remained unchanged during the 24-hour storage period. The e.e. value of the compound solution at low concentration (0.004 mg/mL) was not measured since its low content did not meet the requirements of the method.

7) The above results showed that under the conditions of natural light and room temperature (25±3° C.), it would be best to use the compound solutions (concentration range: 0.004 mg/mL to 0.94 mg/mL) of the AST-3424 injections (1 mL:10 mg preparation) and 5% glucose injections (adjusted to pH7.4) within 8 h.

As could be appreciated from the experimental conclusion derived from the above experiments that the AST-3424 solution was stable under alkaline pH conditions, when compounding, the 5% glucose injection (the pH ranged from 3.2 to 6.5 as prescribed in the pharmacopoeia) or normal saline (the pH ranged from 4.5 to 7.0 as prescribed in the pharmacopoeia) must be firstly added with an alkaline solution such as $NaHCO_3$ solution to adjust the pH value to 6.8-10.5 (preferably, the resulting solution was alkaline), preferably pH 7.4, so that the concentrated AST-3424 injection preparation added subsequently could be formulated into a qualified injection for on-site use.

The invention claimed is:

1. A formulation comprising a solution of an active AST-3424 and a solvent, wherein the solvent comprises a C2-C8 monohydric alcohol, wherein said solution contains 0.1 to 200 mg/ml of the active AST-3424, and wherein no water is added, and the water content is controlled within 0.5% by mass.

2. The formulation according to claim 1, wherein the solvent further comprises a C2-C8 polyhydric alcohol, and wherein the polyhydric alcohol is a dihydric, trihydric, or hexahydric.

3. The formulation according to claim 1, wherein the solvent further comprises a pharmaceutically suitable water-soluble polymer, and wherein the solvent is a liquid or a semi-liquid.

4. The formulation according to claim 3, wherein the water-soluble polymer is selected from the group consisting of polyethylene glycol, polyvinyl alcohol, polyvinylpyrrolidone, poloxamer, polysorbate, and glucan.

5. The formulation according to claim 2, wherein the C2-C8 polyhydric alcohol is selected from the group consisting of ethylene glycol, propylene glycol, glycerol, mannitol, and sorbitol.

6. The formulation according to claim 1, wherein the solvent is a mixture of:

a) a C2-C4 monohydric alcohol, and b) a C2 or C3 dihydric alcohol.

7. The formulation according to claim 1, wherein the C2-C8 monohydric alcohol is ethanol.

8. The formulation according to claim 1, wherein the solvent is a mixture of ethanol and propylene glycol.

9. The formulation according to claim 1, wherein the C2-C8 monohydric alcohol is not less than 50% by volume in the solvent.

10. The formulation according to claim 1, wherein the solvent is 75% ethanol and 25% propylene glycol, by volume.

11. The formulation according to claim 1, wherein the solution comprises 10 mg/ml of the active AST-3424.

12. A stable AST-3424 preparation product comprising:

a) 0.75 ml of anhydrous ethanol, b) 0.25 ml of anhydrous propylene glycol, and c) 10 mg of an active AST-3424;

wherein the stable AST-3424 preparation product is present in a 2-, 5-, or 10-ml lightproof glass vial made of a neutral borosilicate glass material and charged with a protective gas, and wherein no water is added, and the water content is controlled within 0.5% by mass.

13. A method for preparing formulation, comprising the following steps:

i) mixing and dissolving an active AST-3424 and a first amount of a prescription volume of ethanol to obtain a first dissolution;

ii) dissolving propylene glycol in a prescription volume in the first dissolution of i) to obtain a second dissolution; and iii) dissolving a second amount of a prescription volume of ethanol to obtain a solution containing 0.1 to 200 mg/ml of the active AST-3424, wherein no water is added, and the water content is controlled within 0.5% by mass.

14. A composition formulated for injection, comprising an isotonic solution comprising:

a) an active AST-3424, b) an isotonic regulator, c) ethanol, d) propylene glycol, e) a pH regulator, and f) water;

wherein the pH of the composition is from 6.8 to 10.5.

15. The composition according to claim 14, wherein the active AST-3424 has a concentration of from 0.1 to 200 mg/ml.

16. The composition according to claim 14, wherein the pH regulator is selected from the group consisting of sodium citrate, potassium citrate, sodium acetate, potassium acetate, potassium dihydrogen phosphate, sodium dihydrogen phosphate, dipotassium hydrogen phosphate, disodium hydrogen phosphate, potassium phosphate, sodium phosphate, sodium hydroxide, potassium hydroxide, sodium bicarbonate, potassium bicarbonate, sodium carbonate, potassium carbonate, and any combinations thereof.

17. The composition according to claim 14, wherein the isotonic regulator is selected from the group consisting of sodium chloride, glucose, sucrose, fructose, xylitol, glycerol, sorbitol, mannitol, potassium chloride, mannose, calcium chloride, and magnesium chloride.

18. The method according to claim 13, further comprising the following step:

iv) adding an amount of sodium bicarbonate solution as a pH regulator to a 5% glucose solution so that the pH of the solution is 7.4.

* * * * *